US006617125B2

(12) United States Patent
Adler, Jr.

(10) Patent No.: US 6,617,125 B2
(45) Date of Patent: Sep. 9, 2003

(54) COMPOSITIONS FOR ENHANCED CATALYZED REPORTER DEPOSITION

(75) Inventor: Karl Edwin Adler, Jr., Newburyport, MA (US)

(73) Assignee: PerkinElmer Life Sciences, Inc., Boston, MA (US)

( * ) Notice: Subject to any disclaimer, the term of this patent is extended or adjusted under 35 U.S.C. 154(b) by 0 days.

(21) Appl. No.: 09/895,937

(22) Filed: Jun. 29, 2001

(65) Prior Publication Data

US 2003/0017460 A1 Jan. 23, 2003

(51) Int. Cl.$^7$ ................................................ C12Q 1/28
(52) U.S. Cl. ......................... 435/28; 435/968; 435/975
(58) Field of Search ........................... 435/28, 188, 968, 435/975; 436/172

(56) References Cited

U.S. PATENT DOCUMENTS

| | | | |
|---|---|---|---|
| 4,521,511 A | 6/1985 | Stout ............................. | 435/28 |
| 4,598,044 A | 7/1986 | Kricka et al. ................... | 435/28 |
| 4,729,950 A | 3/1988 | Kricka et al. ................... | 435/28 |
| 5,196,306 A | 3/1993 | Bobrow et al. ............... | 435/7.9 |
| 5,356,893 A * | 10/1994 | Bradshaw et al. ........ | 514/227.2 |
| 5,467,287 A | 11/1995 | Wenner et al. .............. | 548/455 |
| 5,583,001 A | 12/1996 | Bobrow et al. .............. | 435/7.5 |
| 5,629,168 A * | 5/1997 | Kricka .......................... | 435/28 |
| 5,688,966 A | 11/1997 | Bobrow et al. .............. | 548/455 |
| 5,731,158 A | 3/1998 | Bobrow et al. .............. | 435/7.5 |
| 5,835,101 A | 11/1998 | Otsuka .......................... | 435/28 |
| 5,863,748 A | 1/1999 | Bobrow ........................ | 435/28 |
| 6,372,937 B1 * | 4/2002 | Bobrow et al. .............. | 562/444 |

OTHER PUBLICATIONS

Hark R. Novel Approaches Toward Ninhydrin Analogs. Tetrahedron Letters 35(42)7719–7722, 1994.*
Whitaker, et al., Modification of Enzymic Activity, II. Effects of Salts on A–Amylase, Alcohol Dehydrogenase, Peroxide and Hematin Catalysis, Nov. 15, 1961, pp. 310–317.
The Journal of Histochemistry and Cytochemistry, Imidazole Increases the Sensitivity of the Cytochemical Reaction for Peroxidase with Diaminobenzidine at a Neutral pH, vol. 30, No. 5, pp. 491–493, 1982.
Bohrow et al., Catalyzed Reporter Deposition, A Novel Method of Signal Amplification, II. Application to Membrane Immunoassays, Oct. 30, 1990, pp. 103–112.
Bobrow et al., Catalyzed Reporter Deposition, A Novel Method of Signal Amplification, Application to Immunoassays, Sep. 26, 1989, pp. 279–285.
Zaitsu et al., New Fluorogenic Substrates for Horseradich Peroxidase: Rapid and Sensitive Assays for Hydrogen Peroxide and the Peroxidase, May 29, 1980, pp. 109–113.

Resmini et al., Preparation by pH–Dependence and Chemical Modification Studies: Evidence for the Involvement of Tyr and Arg Side Chains as Hydrogen–Bond Donors, Apr. 7, 1997, pp. 279–287.
Rao et al., Studies Directed Towards the Total Synthesis of Vancomycin: Formation of Biphenyl Ether by Macrocyclisation, Sep. 9, 1994, pp. 8465–8468.
Tacker et al., Effect of Tranylcypromine Sulphate on the Metabolism of [14C]Tyramine in vivo in the Rat, Nov. 18, 1971, pp. 245–246.
Tanaka et al., Gas–Chromatographic Method of Analysis for Urinary Organic Acids. I. Retention Indices of 155 Metabolically Important Compounds, vol. 26, No. 13, 1980, pp. 1839–1846.
De Jong, et al., Sensitivity of Various Visualization Methods for Peroxidase AMD Alkaline Phosphatase Activity in Immunoenzyme Histochemistry, Jun. 10, 1985, pp. 1119–1130.

* cited by examiner

Primary Examiner—Ralph Gitomer
(74) Attorney, Agent, or Firm—Gifford, Krass, Groh, Sprinkle, Anderson & Citkowski, P.C.

(57) ABSTRACT

A method for enhancing the conversion of a phenol substrate to a product by a peroxidase enzyme comprises the steps of reacting a conjugate comprising a detectably labeled phenol-containing molecule with a peroxidase enzyme in the presence of an enhancing reagent, the enhancing reagent comprising an organic compound having the structure

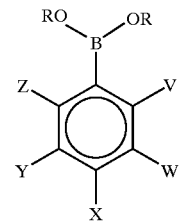

wherein each R is independently selected from the group consisting of: hydrogen and a $C_{1-12}$ substituent; where V, W, Y and Z are each independently selected from the group consisting of: H, halogen, the $C_{1-12}$ substituent, $NR_2$, OR and SR; and where X is selected from the group consisting of: H, Br, Cl, F, the $C_{1-12}$ substituent, $NR_2$, OR and SR; or synergistic mixtures of an inorganic salt and the organic compound. The $C_{1-12}$ substituent is linear, branched or cyclic. The $C_{1-12}$ substituent is alkyl, alkenyl, alkynyl, heteroatom substituted alkyl, heteroatom substituted alkenyl, heteroatom substituted alkynyl, aryl, arylalkyl, arylalkenyl or arylalkynyl. Further, the heteroatom is N, O, S or halogen. Any C, N, O or S in the $C_{1-12}$ substituent optionally has a pendant moiety which is carbonyl, hydroxyl, carboxyl, amine, thiol, thioester, thioether, phosphate, alkoxy, aryl, arylalkyl, sulfonamide or alkyl halide. A kit is provided containing an enhancing reagent for enhancing the detection of an enzyme reaction as described herein, together with instructions for use.

27 Claims, 2 Drawing Sheets

(2 of 2 Drawing Sheet(s) Filed in Color)

Figure 1 A-G
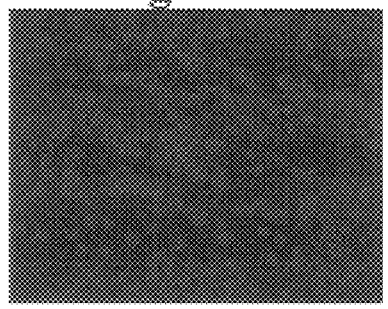
A) Unenhanced
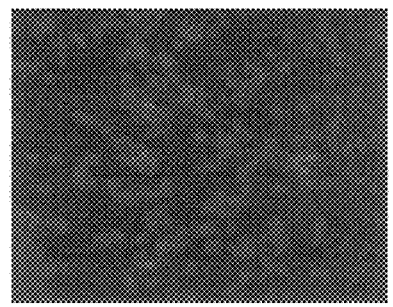
B) p-Fluoro BA
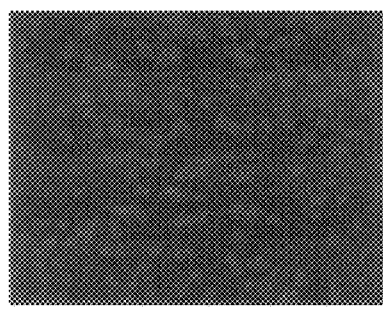
C) m-Fluoro BA
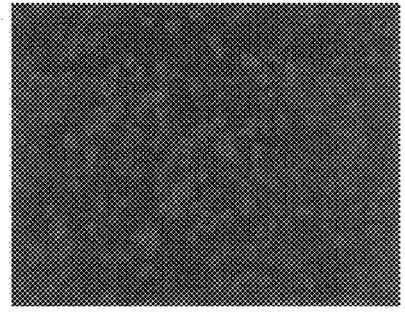
D) p-Chloro BA
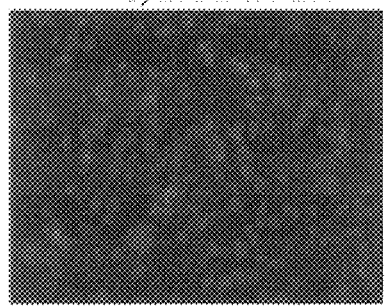
E) m-Chloro BA
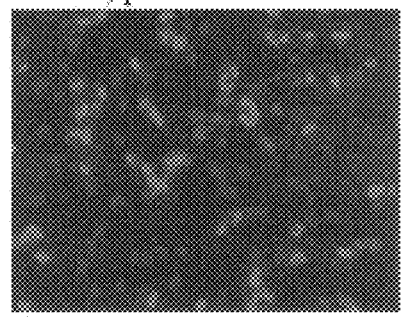
F) p-Bromo BA
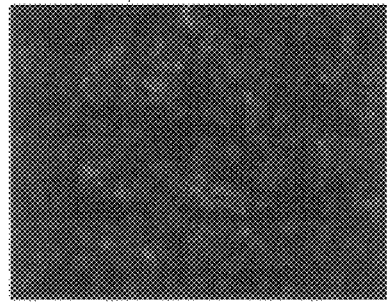
G) m-Iodo BA A) Unenhanced
B) p-Bromo BA
C) p-Acetyl BA
D) p-Thioanisole BA

COMPOSITIONS FOR ENHANCED CATALYZED REPORTER DEPOSITION

FIELD OF THE INVENTION

This invention relates to enzymatic assays, and more particularly to enhancers for use in catalyzed reporter deposition.

BACKGROUND OF THE INVENTION

Peroxidase, because of its high turnover rate, good stability, and availability is widely used in enzyme-based analytical methods. For example, horseradish peroxidase (HRP) (EC 1.11.1.7) catalyzes the oxidation of a large variety of hydrogen-donating substrates with hydrogen peroxide. HRP is also one of the preferred enzymes for use in catalyzed reporter deposition.

Catalyzed reporter deposition (CARD) is a novel method of signal amplification which constitutes the subject matter of U.S. Pat. Nos. 5,863,748; 5,688,966; 5,767,287; 5,731,158; 5,583,001 and 5,196,306. It is also discussed in Bobrow et al., *Journal of Immunological Methods*, 125: 279–285 (1989) and in Bobrow et al., *Journal of Immunological Methods*, 137: 103–112(1991).

The method utilizes an analyte-dependent enzyme activation system ("ADEAS") to catalyze the deposition of a detectable label onto the solid phase of an assay platform. These enzymatically deposited labels may be detected directly or indirectly and results in signal amplification and improved detection limits. In a preferred embodiment, HRP is the enzyme.

HRP reacts with a conjugate consisting of a detectably labeled substrate specific for the ADEAS. When the ADEAS and the conjugate react, an activated conjugate is formed which deposits covalently wherever receptor site for the activated conjugate is immobilized.

For analytical use, substrate oxidation by HRP has been used to generate products which become colored, fluorescent or chemiluminescent. These products either remain soluble or become insoluble and precipitate on the solid phase. The CARD method differs in this respect as the products of the detectably labeled phenol substrate become covalently bound to the solid phase.

To improve detection limits in analytical methods, it is desirous to increase or enhance the substrate to product conversion by enzymes. Although a substance which enhances HRP catalysis regardless of the substrate used has not been discovered, several enhancers specific for HRP substrates which form soluble products have been described. One enhancer specific for the substrate diaminobenzidine, which forms an insoluble product has been described. Enhancers for substrates which, by the catalytic activity of HRP, form covalently depositable products have not been described.

J. R. Whitaker and A. L. Tappel, *Biochimica et Biophysica Acta*, pages 310–317, Vol. 62, 1962 show that KCl, NaCl, $Na_2SO_4$ and to a lesser extent, LiCl enhance the oxidation of guaiacol.

U.S. Pat. No. 4,598,044 issued to Kricka et al. on Jul. 1, 1986 describes the enhancement of the HRP catalyzed oxidation of the substrate, 2,3-dihydro-1,4-phthalazinedione, which forms a soluble chemiluminescent product, by various phenolic compounds.

U.S. Pat. No. 4,729,950 issued to Kricka et al. on Mar. 8, 1988 describes the enhancement of the HRP catalyzed oxidation of the substrate, 2,3-dihydro-1,4-phthalazinedione, by various aromatic amine compounds. Tables 1 and 2 summarize various substrate/enhancer combinations. The Tables and the discussion (column 3 line 67 to column 4 line 34) lead to the conclusion that whether an HRP catalyzed oxidation of a substrate will be enhanced by a given compound is not predictable.

U.S. Pat. No. 5,629,168 issued to Kricka on May 13, 1997 describes the enhancement of the HRP catalyzed oxidation of the substrate, 2,3-dihydro-1,4-phthalazinedione, by aromatic organoboron compounds.

U.S. Pat. No. 4,521,511 issued to Stout on Jun. 4, 1985 describes the enhancement of the HRP catalyzed oxidation of the substrate, 2,2'-azino-di(3-ethyl-benzothiazolone-6-sulfonic acid), by various phenolic compounds.

W. Straus, *Journal of Histochemistry and Cytochemistry*, Vol. 30, pages 491–493, 1982, shows that imidazole enhances the HRP catalyzed oxidation of diaminobenzidine which forms in insoluble product.

A. S. H. de Jong et al., *Histochemical Journal*, Vol. 17, pages 1119–1130, 1985 also show that imidazole enhances the oxidation of diaminobenzidine by approximately four fold, a substrate combination of p-phenylenediamine-pyrocatechol by two fold and has no effect on the substrate 4-chloro-1-naphthol, all of which form insoluble products.

The aforementioned enhancers, with the exception of imidazole, only enhance the conversion of soluble substrates to soluble products. In addition, the enhancers are substrate specific. The KCl, NaCl, $Na_2SO_4$ and LiCl enhancement of the oxidation of guaiacol is specific for guaiacol. These salts do not enhance the oxidation of substrates which form insoluble products nor do they enhance the oxidation of commonly used substrates that form soluble products, such as orthophenylediamine or tetramethylbenzidine. The enhancers for 2,3-dihydro-1,4-phthalazinedione also do not enhance the oxidation of substrates which form insoluble products nor do they enhance the oxidation of commonly used substrates that form soluble products, such as orthophenylediamine or tetramethylbenzidine. Imidazole, which has been demonstrated to enhance the oxidization of diaminobenzidine, has a marginal effect on p-phenylenediamine-pyrocatechol, no effect on 4-chloro-1-naphthol, and no effect on substrates which form covalently depositable products. Whether the oxidation of a given substrate by HRP will be enhanced by a given compound cannot be predicted.

Accordingly, it would be advantageous and desirable to have reagents for enhancing the catalysis of HRP and to have an enhancement effect greater than would be expected based on previous technology.

SUMMARY OF THE INVENTION

The present invention concerns enhancing a Catalyzed Reporter Deposition (CARD) method by reacting a conjugate comprising a detectably labeled phenol-containing molecule with a peroxidase enzyme, wherein the reaction is carried out in the presence of an enhancing reagent including, an organic enhancing compound or synergistic mixtures of an inorganic salt and the organic enhancing compound. The organic enhancing reagent has the structure:

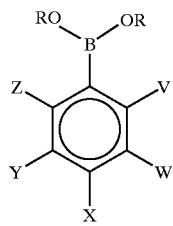

wherein each R is independently selected from the group consisting of: hydrogen and a $C_{1-12}$ substituent; where V, W, Y and Z are each independently selected from the group consisting of: H, halogen, the $C_{1-12}$ substituent, $NR_2$, OR and SR; and where X is selected from the group consisting of: H, Br, Cl, F, the $C_{1-12}$ substituent, $NR_2$, OR and SR; or synergistic mixtures of an inorganic salt and the organic compound. The $C_{1-12}$ substituent is linear, branched or cyclic. The $C_{1-12}$ substituent is alkyl, alkenyl, alkynyl, heteroatom substituted alkyl, heteroatom substituted alkenyl, heteroatom substituted alkynyl, aryl, arylalkyl, arylalkenyl or arylalkynyl. Further, the heteroatom is N, O, S or halogen. Any C, N, O or S in the $C_{1-12}$ substituent optionally has a pendant moiety which is carbonyl, hydroxyl, carboxyl, amine, thiol, thioester, thioether, phosphate, alkoxy, aryl, arylalkyl, sulfonamide or alkyl halide.

A kit is provided containing an enhancing reagent for enhancing the detection of an enzyme reaction as described herein, together with instructions for use.

BRIEF DESCRIPTION OF THE DRAWINGS

The file of this patent contains at least one drawings executed in color.

FIGS. 1A–G are photographs illustrating Enhanced Catalyzed Reporter Deposition (CARD) detection using cyanine-3 tyramide wherein different enhancers are used: (A) no enhancer, (B) p-fluoro boronic acid, (C) m-fluoro boronic acid, (D) p-chloro boronic acid, (E) m-chloro boronic acid, (F) p-bromo boronic acid, and (G) m-iodo boronic acid.

DETAILED DESCRIPTION OF THE INVENTION

Figure 2:
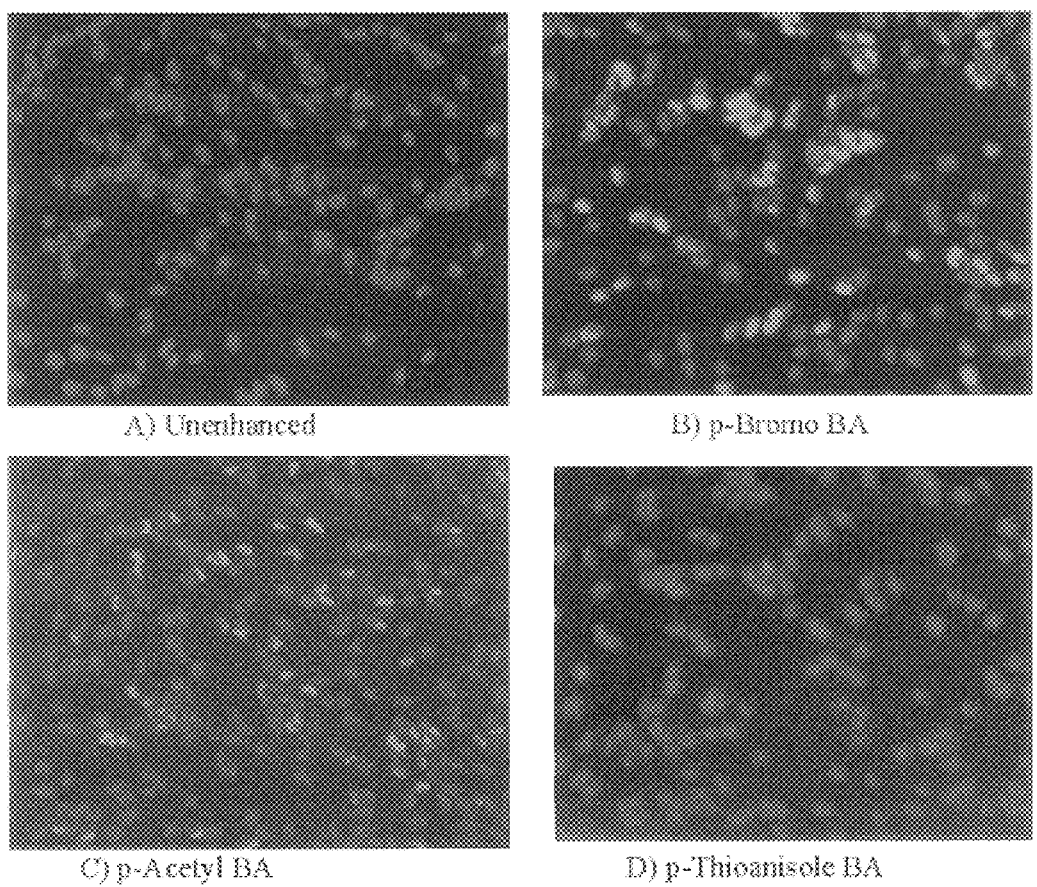
FIGS. 2A–D are photographs illustrating Enhanced Catalyzed Reporter Deposition (CARD) detection using cyanine-3 tyramide wherein different enhancers are used: (A) no enhancer, (B) p-bromo boronic acid, (C) p-acetyl boronic acid and (D) p-thioanisole boronic acid.

The present invention relates to enhancing the catalysis of HRP in a CARD or tyramide signal amplification (TSA) method by reacting a conjugate comprising a detectably labeled phenol-containing molecule with a peroxidase enzyme, wherein the reaction is carried out in the presence of an enhancing reagent which is an organic enhancing compound or synergistic mixtures of an inorganic salt such as NaCl, $MgCl_2$, KCl, $CaCl_2$, sodium phosphate, sodium acetate, ammonium acetate and ammonium sulfate and the organic enhancing reagents.

Organic compounds useful as enhancing reagents are of the structure

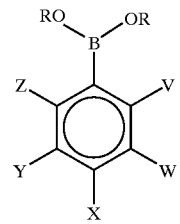

wherein each R is independently selected from the group consisting of: hydrogen and a $C_{1-12}$ substituent; where V, W, Y and Z are each independently selected from the group consisting of: H, halogen, the $C_{1-12}$ substituent, $NR_2$, OR and SR; and where X is selected from the group consisting of: H, Br, Cl, F, the $C_{1-12}$ substituent, $NR_2$, OR and SR; or synergistic mixtures of an inorganic salt and the organic compound. The $C_{1-12}$ substituent is linear, branched or cyclic. The $C_{1-12}$ substituent is alkyl, alkenyl, alkynyl, heteroatom substituted alkyl, heteroatom substituted alkenyl, heteroatom substituted alkynyl, aryl, arylalkyl, arylalkenyl or arylalkynyl. Further, the heteroatom is N, O, S or halogen. Any C, N, O or S in the $C_{1-12}$ substituent optionally has a pendant moiety which illustratively include carbonyl, hydroxyl, carboxyl, amine, thiol, thioester, thioether, phosphate, alkoxy, aryl, arylalkyl, sulfonamide or alkyl halide Broadly, the concentration of the inorganic enhancing reagent ranges from approximately 0.1 M (molar) to saturation. The concentration of the inorganic enhancing reagent preferably is at least approximately 0.5 M. Most preferably, the concentration of the inorganic enhancing reagent ranges from approximately at least 2 M to saturation.

The concentration of the organic enhancing reagent preferably ranges between approximately $1 \times 10^{-6}$ M and $1 \times 10^{-1}$ M. More preferably, the concentration of the organic enhancing reagent ranges from approximately $1 \times 10^{-5}$ M to $1 \times 10^{-2}$ M.

Preferred organic enhancing reagents are p-fluoro boronic acid, m-fluoro boronic acid, p-chloro boronic acid, m-chloro boronic acid, p-bromo boronic acid, m-iodo boronic acid and compounds of the structures:

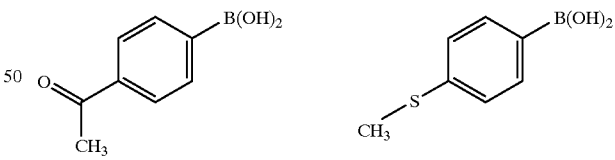

4-Acetylphenyl boronic acid (p-Acetylphenyl boronic acid)     4-Thioanisole boronic acid (p-Thioanisole boronic acid)

As used herein, the term conjugate means a detectably labeled phenol-containing molecule which is a substrate for the HRP enzyme. Preferred substrates include tyramide compounds and p-hydroxycinnamic acid compounds. Derivatives of tyramide compounds and p-hydroxycinnamic acid compounds as described in, for example, U.S. Pat. Nos. 5,196,306 and 5,863,748 are also preferred substrates.

The conjugate therefore comprises two components. One component is the phenol-containing molecule which serves as the substrate for the enzyme. The other component is the detectable label. As used herein, detectably labeled means that the substrate can be coupled to either a reporter or to an unlabeled first member of a specific binding pair. When the substrate is coupled to an unlabeled member of a specific binding pair, following covalent binding of the activated conjugate, the substrate-specific binding pair complex is reacted with the second member of the binding pair which is coupled to a reporter. Illustrative examples of reporters are enzymes, radioactive isotopes, fluorogenic, chemiluminescent, or electrochemical materials or a member of a specific binding pair. A preferred conjugate is cyanine-3 tyramide.

As used herein, the term receptor site means a site at which the activated conjugate will bind to the surface through the formation of a covalent bond. Examples of receptor site compositions for phenolic substrates include tyrosine residues of proteins, phenol and other electron rich organic molecules. The receptor sites may be reactive components of the surface of a solid support or may be added to the surface of the solid support.

As used herein, the term activated conjugate means the conjugate has been primed to bind to the receptor site.

As used herein, the term halogen includes chlorine, fluorine, bromine, and iodine.

As used herein, the term alkyl means a straight or branched chain hydrocarbon. Representative examples of alkyl groups are methyl, ethyl, propyl, isopropyl, isobutyl, butyl, tert-butyl, sec-butyl, pentyl, and hexyl.

As used herein, the term heteroatom includes oxygen, nitrogen, sulfur and halogen.

Members of specific binding pairs suitable for use in practicing the invention can be of the immune or non-immune type. Immune specific binding pairs are exemplified by antigen/antibody systems or hapten/anti-hapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab type fragments which are defined as fragments devoid of the Fc portion, e.g., Fab, Fab' and F(ab')2 fragments, or may be so-called "half molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, receptor-ligand, toxin—toxin binding protein and lectin-oligosaccharide. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino) benzoic acid (DMAB).

As used herein, the term enhancing reagent means a reagent which increases or accelerates the rate of binding of the activated conjugate to the receptor site. The increased or accelerated binding of the activated conjugate to the receptor site is monitored directly or indirectly from the detectable label of the conjugate.

An unexpected aspect of the present invention relates to the molecular nature of the enhancer moieties in relation to the detectably labeled substrate. Two reactions are required to allow the conjugate to bind to the receptor site. First, the peroxidase enzyme catalyzes the oxidation, or activation of the conjugate; second, the activated conjugate reacts with the receptor site, forming a covalent bond. The structures of the organic enhancers lend themselves as substrates for HRP and/or receptor sites for the activated conjugate. Therefore, one would predict that these moieties would act as inhibitors of either the first, the second, or both reactions rather than as enhancers.

The present invention further relies on a synergistic effect between inorganic salts and organic enhancers.

The present invention further includes a kit containing an enhancing reagent for enhancing the detection of an enzyme reaction as described herein, together with instructions for use.

EXAMPLE 1

Detection of Cytomegalovirus (CMV) Using Cyanine-3 Tyramide Enhanced with Para and Meta Halogen Phenyl Boronic Acids Eight well slides with MRC-5 cells infected with CMV, available from Hemagen Diagnostics, Inc., are hydrated with phosphate buffered saline (PBS) for two minutes. An anti-CMV-horseradish peroxide is prepared by a modification of the method of Ishikawa, E., et al., *J. Immunoassay*, 209–237, 1983. The anti-CMV-horseradish peroxide is diluted in 0.1 M tris, 0.15 M NaCl, 0.5% casein, pH 7.5 and incubated on the slide at room temperature for 30 minutes. The slide is then washed with 0.1 M tris, 0.15 M NaCl, 0.05% Tween 20, pH 7.5 (TNT) buffer for two minutes. This wash is repeated two additional times. Cyanine-3 tyramide is diluted to 2 µg/ml in 1× Amplification Diluent available from PerkinElmer Life Sciences, FP-485, containing: A) no additive, B) p-fluoro boronic acid (Frontier Scientific, Inc., Logan, Utah) at 20 µg/ml, C) m-fluoro boronic acid (Frontier Scientific, Inc.) at 20 µg/ml, D) p-chloro phenyl boronic acid (Frontier Scientific, Inc.) at 20 µg/ml, E) m-chloro boronic acid (Frontier Scientific, Inc.) at 20 µg/ml, F) p-bromo boronic acid (Frontier Scientific, Inc.) at 20 µg/ml, G) m-iodo boronic acid (Frontier Scientific, Inc.) at 20 µg/ml, and H) o-iodo boronic acid (Frontier Scientific, Inc.) at 20 µg/ml. Each of these solutions is applied to one of the wells on a CMV slide and incubated for ten minutes at room temperature. The slide is washed in TNT three times for five minutes each. Counterstaining of the slide is performed by incubating with DAPI at 5 µg/ml in TNT for five minutes. The slide is rinsed in TNT and then deionized water.

FIG. 1 shows that the addition of various enhancer compounds enhance the deposition of cyanine-3 tyramide by horseradish peroxidase.

EXAMPLE 2

Detection of Cytomegalovirus (CMV) Using Cyanine-3 Tyramide Enhanced with Para Halogen and Alkyl Phenyl Boronic Acids Eight well slides with MRC-5 cells infected with CMV, available from Hemagen Diagnostics, Inc., are hydrated with phosphate buffered saline (PBS) for two minutes. An anti-CMV-horseradish peroxide is prepared by a modification of the method of Ishikawa, E., et al., *J. Immunoassay*, 209–237, 1983. The anti-CMV-horseradish peroxide is diluted in 0.1 M tris, 0.15 M NaCl, 0.5% casein, pH 7.5 and incubated on the slide at room temperature for 30 minutes. The slide is then washed with 0.1 M tris, 0.15 M NaCl, 0.05% Tween 20, pH 7.5 (TNT) buffer for two minutes. This wash is repeated two additional times. Cyanine-3 tyramide is diluted to 2 μg/ml in 1× Amplification Diluent (PerkinElmer Life Sciences, FP-485) containing A) no additive, B) p-iodo boronic acid (Frontier Scientific, Inc.) at 20 μg/ml, C) p-bromo boronic acid (Frontier Scientific, Inc.) at 20 μg/ml, D) p-acetyl boronic acid (Frontier Scientific, Inc.) at 20 μg/ml, and E) p-thioanisole boronic acid (Frontier Scientific, Inc.) at 20 μg/ml. Each of these solutions is applied to one of the wells on a CMV slide and incubated for ten minutes at room temperature. The slide is washed three times in TNT for five minutes each. Counterstaining of the slide is performed by incubating with DAPI at 5 μg/ml in TNT for five minutes. The slide is rinsed in TNT and then deionized water.

FIG. 2 shows that the addition of various enhancer compounds enhance the deposition of cyanine-3 tyramide by horseradish peroxide.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for enhancing detection of an enzyme reaction, the method comprising the step of:

reacting a conjugate comprising a detectably labeled phenol-containing molecule with a peroxidase enzyme in the presence of an enhancing reagent solution, the enhancing reagent solution comprising: an organic compound having the structure:

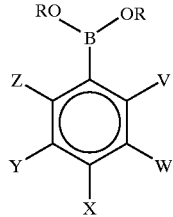

wherein each R is independently selected from the group consisting of: hydrogen and a $C_{1-12}$ substituent; where V, W, Y and Z are each independently selected from the group consisting of: H, halogen, the $C_{1-12}$ substituent, $NR_2$, OR and SR; and where X is selected from the group consisting of: H, Br, Cl, F, the $C_{1-12}$ substituent, $NR_2$, OR and SR; or synergistic mixtures of an inorganic salt and the organic compound.

2. The method according to claim 1 wherein the $C_{1-12}$ substituent is selected from the group consisting of: linear, branched and cyclic.

3. The method according to claim 1 wherein the $C_{1-12}$ substituent is selected from the group consisting of: alkyl, alkenyl, alkynyl, heteroatom substituted alkyl, heteroatom substituted alkenyl, heteroatom substituted alkynyl, aryl, arylalkyl, arylalkenyl, arylalkynyl.

4. The method according to claim 3 wherein the heteroatom is selected from N, O, S and halogen.

5. The method according to claim 1 wherein any atom in the $C_{1-12}$ substituent has a pendant moiety selected from the group consisting of: carbonyl, hydroxyl, carboxyl, amine, thiol, thioester, thioether, phosphate, alkoxy, aryl, arylalkyl, sulfonamide and alkyl halide.

6. The method according to claim 1 wherein the inorganic salt is selected from the group consisting of: NaCl, $MgCl_2$, KCl, and $CaCl_2$, sodium phosphate, sodium acetate, ammonium acetate, and ammonium sulfate.

7. The method according to claim 1 wherein the peroxidase enzyme is horseradish peroxidase.

8. The method according to claim 1 wherein the concentration of the inorganic salt ranges from 0.5 molar to saturation.

9. The method according to claim 1 wherein the concentration of inorganic salt ranges from approximately 2 molar to saturation.

10. The method according to claim 1 wherein the concentration of the organic compound ranges from approximately $1\times10^{-6}$ molar to $1\times10^{-1}$ molar.

11. The method according to claim 1 wherein the concentration of the organic compound ranges from approximately $1\times10^{-5}$ molar to $1\times10^{-2}$ molar.

12. The method according to claim 1 wherein the phenol-containing molecule is selected from the group consisting of: a tyramine compound and a p-hydroxycinnamoyl compound.

13. The method according to claim 1 wherein said detectably labeled phenol-containing molecule is deposited onto a solid phase of an array platform.

14. A kit for detection of an enzyme reaction, the kit comprising:

a conjugate comprising a detectably labeled phenol-containing molecule; and an enhancing reagent for enhancing the detection of the enzyme reaction, said enhancing reagent comprising an organic compound having the structure:

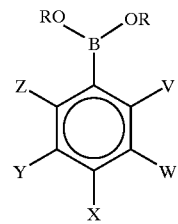

wherein each R is independently selected from the group consisting of: hydrogen and a $C_{1-12}$ substituent; where V, W, Y and Z are each independently selected from the group consisting of: H, halogen, the $C_{1-12}$ substituent, $NR_2$, OR and SR; and where X is selected from the group consisting of: H, Br, Cl, F, the $C_{1-12}$ substituent, $NR_2$, OR and SR; or synergistic mixtures of an inorganic salt and the organic compound.

15. The kit according to claim 14 wherein the $C_{1-12}$ substituent is selected from the group consisting of: linear, branched and cyclic.

16. The kit according to claim 14 wherein the $C_{1-12}$ substituent is selected from the group consisting of: alkyl, alkenyl, alkynyl, heteroatom substituted alkyl, heteroatom substituted alkenyl, heteroatom substituted alkynyl, aryl, arylalkyl, arylalkenyl, arylalkynyl.

17. The kit according to claim 16 wherein the heteroatom is selected from N, O, S and halogen.

18. The kit according to claim 14 wherein any atom in the $C_{1-12}$ substituent has a pendant moiety selected from the group consisting of: carbonyl, hydroxyl, carboxyl, amine, thiol, thioester, thioether, phosphate, alkoxy, aryl, arylalkyl, sulfonamide and alkyl halide.

19. A kit according to claim 14 wherein the inorganic salt is selected from the group consisting of: NaCl, $MgCl_2$, KCl, and $CaCl_2$, sodium phosphate, sodium acetate, ammonium acetate, and ammonium sulfate.

20. A kit according to claim 14 wherein the phenol-containing molecule is selected from the group consisting of: a tyramine compound and a p-hydroxycinnamoyl compound.

21. The kit according to claim 14 wherein said detectably labeled phenol-containing molecule deposits onto a solid phase of an array platform following reaction with a peroxidase enzyme.

22. A kit for enhancing detection of an enzyme reaction, the kit comprising:

instructions for use; and an enhancing reagent for enhancing the detection of the enzyme reaction, said enhancing reagent comprising an organic compound having the structure:

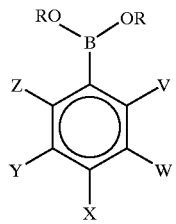

wherein each R is independently selected from the group consisting of: hydrogen and a $C_{1-12}$ substituent; where V, W, Y and Z are each independently selected from the group consisting of H, halogen, the $C_{1-12}$ substituent, $NR_2$, OR and SR; and where X is selected from the group consisting of: H, Br, Cl, F, the $C_{1-12}$ substituent, $NR_2$, OR and SR; and synergistic mixtures of an inorganic salt.

23. The kit according to claim 22 wherein the $C_{1-12}$ substituent is selected from the group consisting of: alkyl, alkenyl, alkynyl, heteroatom substituted alkyl, heteroatom substituted alkenyl, heteroatom substituted alkynyl, aryl, arylalkyl, arylalkenyl, arylalkynyl.

24. The kit according to claim 23 wherein the $C_{1-12}$ substituent is selected from the group consisting of: linear, branched and cyclic.

25. The kit according to claim 22 wherein the heteroatom is selected from N, O, S and halogen.

26. The kit according to claim 22 wherein any atom in the $C_{1-12}$ substituent has a pendant moiety selected from the group consisting of: carbonyl, hydroxyl, carboxyl, amine, thiol, thioester, thioether, phosphate, alkoxy, aryl, arylalkyl, sulfonamide and alkyl halide.

27. A kit according to claim 22 wherein the inorganic salt is selected from the group consisting of: NaCl, $MgCl_2$, KCl, and $CaCl_2$, sodium phosphate, sodium acetate, ammonium acetate, and ammonium sulfate.

* * * * *